United States Patent [19]

Samejima et al.

[11] Patent Number: 5,607,912

[45] Date of Patent: Mar. 4, 1997

[54] HYDROCHLOROFLUOROCARBON AZEOTROPIC OR AZEOTROPIC-LIKE MIXTURE

[75] Inventors: Shunichi Samejima, Tokyo; Kenroh Kitamura, Fujisawa; Naohiro Watanabe, Chiba; Teruo Asano, Yokohama; Toru Kamimura, Ichihara; Yoko Usami, Yokohama, all of Japan

[73] Assignee: Asahi Glass Company Ltd., Tokyo, Japan

[21] Appl. No.: 942,328

[22] Filed: Sep. 9, 1992

Related U.S. Application Data

[63] Continuation of Ser. No. 573,120, Sep. 13, 1990, abandoned.

[30] Foreign Application Priority Data

| Feb. 1, 1989 | [JP] | Japan | 1-20883 |
| Feb. 1, 1989 | [JP] | Japan | 1-20887 |
| Feb. 1, 1989 | [JP] | Japan | 1-20888 |
| Feb. 2, 1989 | [JP] | Japan | 1-22532 |
| Feb. 2, 1989 | [JP] | Japan | 1-22539 |
| Feb. 2, 1989 | [JP] | Japan | 1-22549 |
| Feb. 6, 1989 | [JP] | Japan | 1-25642 |
| Feb. 6, 1989 | [JP] | Japan | 1-25643 |
| Feb. 6, 1989 | [JP] | Japan | 1-25686 |
| Feb. 6, 1989 | [JP] | Japan | 1-25687 |
| Feb. 6, 1989 | [JP] | Japan | 1-25688 |
| Feb. 14, 1989 | [JP] | Japan | 1-32834 |
| Apr. 26, 1989 | [JP] | Japan | 1-104650 |
| Apr. 26, 1989 | [JP] | Japan | 1-104651 |
| May 26, 1989 | [JP] | Japan | 1-131531 |
| May 30, 1989 | [JP] | Japan | 1-134606 |
| May 30, 1989 | [JP] | Japan | 1-134607 |
| Jun. 30, 1989 | [JP] | Japan | 1-167107 |
| Aug. 14, 1989 | [JP] | Japan | 1-207842 |
| Aug. 14, 1989 | [JP] | Japan | 1-207843 |
| Aug. 15, 1989 | [JP] | Japan | 1-209684 |
| Sep. 12, 1989 | [JP] | Japan | 1-234602 |
| Sep. 12, 1989 | [JP] | Japan | 1-234603 |
| Sep. 12, 1989 | [JP] | Japan | 1-234604 |
| Sep. 12, 1989 | [JP] | Japan | 1-234605 |
| Oct. 6, 1989 | [JP] | Japan | 1-260164 |
| Oct. 6, 1989 | [JP] | Japan | 1-260165 |

[51] Int. Cl.$^6$ .......................... C11D 7/50; C23G 5/028; C07C 19/08

[52] U.S. Cl. .......................... 510/411; 510/410; 510/412; 510/408; 510/177; 510/176; 510/415; 252/305; 252/364; 252/67; 203/67

[58] Field of Search .......................... 252/162, 170, 252/171, 172, 305, 364, DIG. 9, 67; 203/67; 510/410, 411, 412, 408, 177, 176, 415

[56] References Cited

U.S. PATENT DOCUMENTS

| 2,683,093 | 7/1954 | Eberl | 252/364 |
| 3,080,430 | 3/1963 | Cohen | 260/653 |
| 3,476,819 | 11/1969 | Trischler | 260/653 |
| 3,804,769 | 4/1974 | Lomas | 510/411 X |
| 3,936,387 | 2/1976 | Reusser | 252/171 |
| 4,654,160 | 3/1987 | Wilson | 510/178 |
| 4,873,021 | 10/1989 | Gorski et al. | 252/364 |
| 4,947,881 | 8/1990 | Magia et al. | 134/40 |
| 4,961,869 | 10/1990 | Eggers et al. | 252/170 |
| 4,970,013 | 11/1990 | Merchant | 252/67 |
| 4,985,168 | 1/1991 | Ohmore et al. | 252/67 |
| 4,988,455 | 1/1991 | Magia et al. | 252/171 |
| 4,995,908 | 2/1991 | Buchwald et al. | 252/171 |
| 5,102,563 | 4/1992 | Desbiendras et al. | 252/171 |
| 5,104,565 | 4/1992 | Magia et al. | 252/171 |
| 5,106,526 | 4/1992 | Magia et al. | 252/171 |
| 5,116,426 | 5/1992 | Asano et al. | 134/40 |
| 5,116,525 | 5/1992 | Merchant | 252/171 |
| 5,116,526 | 5/1992 | Magia et al. | 252/172 |
| 5,118,437 | 6/1992 | Magia et al. | 252/171 |
| 5,118,438 | 6/1992 | Magia et al. | 252/172 |
| 5,120,462 | 6/1992 | Buchwald et al. | 252/171 |
| 5,124,065 | 6/1992 | Magia et al. | 252/171 |
| 5,135,676 | 8/1992 | Buchwald et al. | 252/171 |

FOREIGN PATENT DOCUMENTS

| 1086450 | 9/1980 | Canada . | |
| 0347924 | 12/1989 | European Pat. Off. . | |
| 374780 | 6/1990 | European Pat. Off. | 252/364 |
| 0382095 | 8/1990 | European Pat. Off. . | |
| 2128555 | 10/1972 | France . | |
| 1304195 | 12/1989 | Japan | 252/172 |
| 1301796 | 12/1989 | Japan | 252/172 |
| 1304194 | 12/1989 | Japan | 252/364 |
| 1562026 | 3/1980 | United Kingdom . | |
| 91/05083 | 4/1991 | WIPO . | |
| 91/05082 | 4/1991 | WIPO . | |
| 91/05035 | 4/1991 | WIPO . | |

OTHER PUBLICATIONS

Paleta et al, Collection Czechoslov Chem. Commun vol. 36, 1971 No Month Available pp. 1867–1875.
Patent Abstracts of Japan, vol. 13, No. 124 (C–580) (3472), 27 Mar. 1989, & JP, A, 63295699 (Daikin Ltd) 2 Dec. 1988.
Russian application # 4831377/04 (date unknown).

Primary Examiner—Douglas J. McGinty
Attorney, Agent, or Firm—Oblon, Spivak, McClelland, Maier & Neustadt, P.C.

[57] ABSTRACT

A hydrochlorofluorocarbon azeotropic or azeotropic-like mixture comprising at least one member selected from the group consisting of hydrogen-containing fluoropropanes of the formula I:

$$CH_aCl_bF_cCF_2CH_xCl_yF_z \qquad (I)$$

wherein $a+b+c=3$, $x+y+z=3$, $a+x \geq 1$, $b+y \geq 1$, and $0 \leq a,b,c, x,y,z \leq 3$, and at least one member selected from the group of compounds II consisting of halogenated hydrocarbons having a boiling point of from 20° to 85° C. other than said hydrochlorofluoropropanes, hydrocarbons having a boiling point of from 20° to 85° C. and alcohols having from 1 to 4 carbon atoms.

4 Claims, No Drawings

HYDROCHLOROFLUOROCARBON AZEOTROPIC OR AZEOTROPIC-LIKE MIXTURE

This application is a Continuation of application Ser. No. 07/573,120 filed Sep. 13, 1990, abandoned, which was filed as International Application No. PCT/JP90/00119 on Feb. 1, 1990.

TECHNICAL FIELD

The present invention relates to a novel hydrochlorofluorocarbon azeotropic or azeotropic-like mixture which can be used as a chlorofluorocarbon alternative and which has excellent properties as a solvent and so on.

BACKGROUND ART

Chlorofluorocarbon compounds (hereinafter referred simply as CFCs) have little toxicity and are, in many cases, non-flammable and chemically stable. Various CFCs having different boiling points are available. By virtue of such properties, 1,1,2-trichloro-1,2,2-trifluoroethane (R113) is used as a solvent or a blowing agent; trichloromonofluoromethane (R11) is used as a blowing agent or a propellant; and dichlorodifluoromethane (R12) is used as a propellant or a refrigerant.

Chemically stable R11, R12 and R113 have long lifetime in the troposphere and reach the stratosphere, where they will be dissociated by solar radiation to release chlorine radicals, which initiate a chain reaction with ozone and deplete the ozone layer. Accordingly, the regulations for limiting the use of such conventional CFCs have been implemented. Therefore, a research has been actively conducted to develop a CFC alternative which scarcely depletes the ozone layer.

DISCLOSURE OF THE INVENTION

It is an object of the present invention to provide a mixture containing a novel hydrochlorofluoropropane having 3 carbon atoms, which has various excellent properties equal to conventional CFCs and which is useful as a CFC alternative.

The present invention provides a hydrochlorofluorocarbon azeotropic or azeotropic-like mixture comprising at least one member selected from the group consisting of hydrochlorofluoropropanes of the formula I:

$$CH_aCl_bF_cCF_2CH_xCl_yF_z \qquad (I)$$

wherein $a+b+c=3$, $x+y+z=3$, $a+x \geq 1$, $b+y \geq 1$, and $0 \leq a,b,c,x,y,z \leq 3$, and at least one member selected from the group of compounds II consisting of halogenated hydrocarbons having a boiling point of from 20° to 85° C. other than the above hydrochlorofluoropropanes, hydrocarbons having a boiling point of from 20° to 85° C. and alcohols having from 1 to 4 carbon atoms.

The mixture of the present invention is non-flammable or hardly flammable and may take a form of an azeotropic composition or an azeotropic-like composition. Particularly when used as a solvent, it provides properties equal or superior to conventional 1,1,2-trichlorotrifluoroethane (R113). Therefore, it is very useful as an alternative for R113. Further, no substantial change in the composition was observed when boiling or evaporating. Therefore, it may be used in the same manner as a conventional single CFC, whereby it has a merit in that no substantial change in the conventional technique is required.

BEST MODE FOR CARRYING OUT THE INVENTION

The hydrochlorofluoropropanes of the formula I in the present invention contain a hydrogen atom and a fluorine atom as essential elements and may further contain a chlorine atom. Specifically, they include the following compounds:

$CClF_2CF_2CHCl_2$ (R224ca)
$CCl_2FCF_2CHClF$ (R224cb)
$CF_3CF_2CHCl_2$ (R225ca)
$CClF_2CF_2CHClF$ (R225cb)
$CClF_2CF_3CH_2Cl$ (R234cc)
$CHF_2CF_2CHClF$ (R235ca)
$CH_3CF_2CCl_2F$ (R243cc)
$CHF_2CF_2CH_2Cl$ (R244ca)
$CH_2ClCF_2CH_2Cl$ (R252ca)
$CHCl_2CF_2CH_3$ (R252cb)
$CH_3CF_2CH_2Cl$ (R262ca)
$CHF_2CF_2CCl_2F$ (R225cc)
$CHClFCF_2CHCl_2F$ (R234ca)
$CHF_2CF_2CHCl_2$ (R234cb)
$CH_2FCF_2CCl_2F$ (R234cd)
$CF_3CF_2CH_2Cl$ (R235cb)
$CClF_2CF_2CF_2CH_2F$ (R235cc)
$CH_2ClCF_2CHClF$ (R243ca)
$CH_2FCF_2CHCl_2$ (R243cb)
$CH_2FCF_2CHClF$ (R244cb)
$CClF_2CF_2CH_3$ (R244cc)
$CH_2FCF_2CH_2Cl$ (R253ca)
$CF_3CF_2CHClF$ (R253cb)
$CF_3CF_2CHClF$ (R226ca)
$CClF_2CF_2CHF_2$ (R226cb)
$CCl_3CF_2CHCl_2$ (R222c)
$CCl_2FCF_2CHCl_2$ (R223ca)
$CCl_3CF_2CHClF$ (R223cb)
$CCl_3CF_2CHF_2$ (R224cc)
$CHCl_2CF_2CHCl_2$ (R232ca)
$CCl_3CF_2CH_2Cl$ (R232cb)
$CCl_2FCF_2CH_2Cl$ (R233cb)
$CHCl_2CF_2CHClF$ (R233ca)
$CCl_3CF_2CH_2F$ (R233cc)
$CCl_3CF_2CH_3$ (R242cb)
$CHCl_2CF_2CH_2Cl$ (R242ca)

Among them, preferred are R225ca, R225cb, R244ca, R244cb, R235ca and R243cc.

The halogenated hydrocarbons having a boiling point of from 20° to 85° C. other than the hydrochlorofluoropropanes of the formula I, include chlorinated hydrocarbons, fluorinated hydrocarbons and brominated hydrocarbons having from 1 to 4 carbon atoms.

The chlorinated hydrocarbons having from 1 to 4 carbon atoms, include dichloromethane, trichloromethane, trans-1, 2-dichloroethylene, cis-1,2-dichloroethylene, 1-chloropropane, 2-chloro-2-methylpropane, 1,1,1-trichloroethane and 1,1-dichloroethane. The fluorinated hydrocarbons include 1,1,2-trichlorotrifluoroethane (R113), 1,1,2-trichloro-2,2-difluoroethane (R122), 1,2,2-trichloro-1,2-difluoroethane (R122a), 1,1,1-trichloro-2,2-difluoroethane (R122b), 1,1-dichloro-2,2,2-trifluoroethane (R123), 1,2-dichloro-1,1-difluoroethane (R132b), 1,2-dichloro-1-fluoroethane (R141), 1,1-dichloro-1-fluoroethane (R141b) and trichlorofluoromethane (R11). Likewise, the brominated hydrocarbons include 2-bromopropane as a preferred example.

The hydrocarbons having a boiling point of from 20° to 85° C., include aliphatic, alicyclic and aromatic hydrocarbons. Preferably, they include hydrocarbons having from 5 to 8 carbon atoms such as n-pentane, isopentane, n-hexane, 2,4-dimethylpentane, cyclopentane, 2,2-dimethylbutane, 2-methylpentane, methylcyclopentane, cyclohexane and 2,3-dimethylbutane. The hydrocarbons having from 5 to 8 carbon atoms may be a mixture obtained as a petroleum fraction and may preferably be a petroleum fraction containing as the main component at least one member selected from the group consisting of cyclopentane, 2,2-dimethylbutane, 2-methylpentane and 2,3-dimethylbutane.

The azeotropic or azeotropic-like composition of the mixture of the present invention may vary to an extent of ±1.0% by weight depending upon the purities of the compounds to be mixed or by the influence of measuring error, etc.

To the mixture of the present invention, other components may further be incorporated, as the case requires. For example, when the mixture is used as a solvent, it may contain at least one member selected from the group consisting of hydrocarbons such as neopentane, 3-methylpentane, neohexane, hexane, 3-methylhexane, heptane, isoheptane, 2,3-dimethylpentane, 2,4-dimethylpentane, octane, 2,2,3-trimethylpentane, 2,2,4-trimethylpentane, cyclopentane, methylcyclohexane and ethylcyclohexane; chlorinated hydrocarbons such as 1,1,2-trichloroethane, 1,2-dichloroethane, trichloroethylene and tetrachloroethylene; chlorofluorinated hydrocarbons other than those of the present invention, such as 1,1-dichloro-2,3,3,3-tetrafluoropropene-1, trans-3-chloro- 1,1,1,2,4,4,5,5,5-nonafluoropentene-2, cis-3-chloro-1,1,1,2,4,4,5,5,5-nonafluoropentene-2, 1,1,1,2,2,5, 5,6,6,6-decafluorohexane and tetrachloro-1,2,-difluoroethane; nitro compounds; phenols; amines; ethers; amylenes; esters; organic phosphites; epoxides; furans; alcohols; ketones; amides; and triazoles.

The content of such additional components in the mixture of the present invention is not particularly limited, but for the purpose of improving or controlling the solibility or obtaining a suitable boiling point or non-flammability, the content is usually from 0 to 50% by weight, preferably from 1 to 40% by weight. Preferably such incorporation will bring about an azeotropic or azeotropic-like composition. Further, to give the mixture a high level of stabilizing effect, it is effective to incorporate a stabilizer. The content of such additional components is usually from 1 ppm to 10% by weight, preferably from 10 ppm to 5% by weight. Further, the mixture of the present invention may further contain various cleaning assistants, surfactants, emulsifying agents, water, etc.

As the nitro compounds, those represented by the formula R—$NO_2$ wherein R is a chain or cyclic hydrocarbon group having from 1 to 6 carbon atoms and containing a saturated or unsaturated bond, may be employed. Specifically, they include nitromethane, nitroethane, 1-nitropropane, 2-nitropropane and nitrobenzene. More preferred are nitromethane and nitroethane.

As the phenols, those represented by the following formulas are preferred:

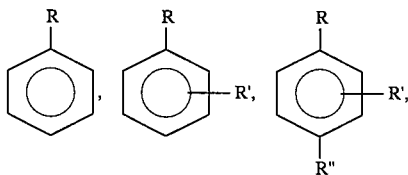

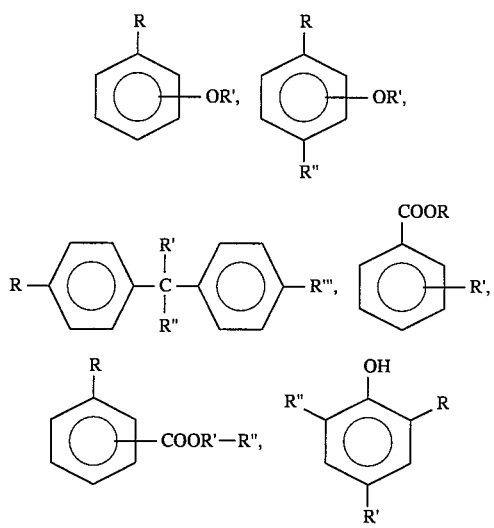

wherein each of R, R', R" and R''' is OH or a chain or cyclic hydrocarbon group having from 1 to 6 carbon atoms and containing a saturated or unsaturated bond.

Specifically, they include phenol, o-cresol, m-cresol, p-cresol, thymol, p-tert-butylphenol, tert-butylcatechol, catechol, isoeugenol, o-methoxyphenol, 4,4'-dihydroxyphenyl-2,2-propane, isoamyl salicylate, benzyl salicylate, methyl salicylate and 2,6-di-t-butyl-p-cresol. More preferred are phenol, 4,4-dihydroxyphenyl-2,2-propane and 2,6-di-t-butyl-p-cresol.

As the amines, those represented by the following formulas are preferred:

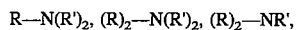

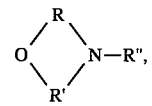

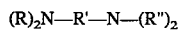

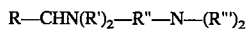

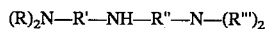

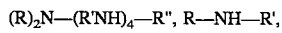

and

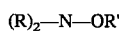

wherein each of R, R', R" and R''' is a hydrogen atom or chain or cyclic hydrocarbon group having from 1 to 8 carbon atoms and containing a Saturated or unsaturated bond.

Specifically, they include pentylamine, hexylamine, diisopropylamine, diisobutylamine, di-n-propylamine, diallylamine, triethylamine, n-methylaniline, pyridine, picoline, morpholine, N-methylmorpholine, triallylamine, allylamine, α-methylbenzylamine, methylamine, dimethylamine, trimethylamine, ethylamine, diethylamine, propylamine, isopropylamine, sec-butylamine, tert-butylamine, dibutylamine, tributylamine, dipentylamine, tripentylamine, 2-ethylhexylamine, aniline, N,N-dimethylaniline, N,N-diethylaniline, ethylenediamine, propylenediamine, diethylenetriamine, tetraethylenepentamine, benzylamine, dibenzylamine, diphenylamine and diethylhydroxylamine. More preferred are diisopropylamine and diallylamine.

As the ethers, those represented by the following formulas are preferred:

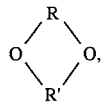

R—OH—R'OH,

HO—R—O—R', HO—R—O—R'—O—R", HO—R—OH,

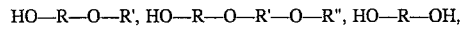

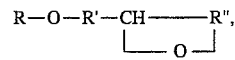

R—O—R'—O—R",

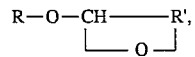

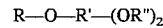

R—O—R'—(OR")₂ wherein each of R, R' and R" is a chain or cyclic hydrocarbon group having from 1 to 10 carbon atoms and containing a saturated or unsaturated bond. Specifically, they include 1,4-dioxane, 1,2-butanediol, isopropyl ether, ethylene glycol monomethyl ether, diethylene glycol monomethyl ether, diethylene glycol monoethyl ether, dipropylene glycol methyl ether, ethyl isobutyl ether, ethyl isopentyl ether, ethyl naphthyl ether, ethyl vinyl ether, ethyl phenyl ether, anisole, anethole, ethyl propargyl ether, ethyl propyl ether, ethyl methyl ether, ethylene glycol, methyl glycidyl ether, ethylene glycol diethyl ether, ethylene glycol diphenyl ether, ethylene glycol dimethyl ether, ethylene glycol monophenyl ether, ethylene glycol monobutyl ether, ethylene glycol monobenzyl ether, dipentyl ether, allyl ethyl ether, diisopentyl ether, diallyl ether, butyl glycidyl ether, allyl glycidyl ether, dipropyl ether, ethyl glycidyl ether, vinyl glycidyl ether, dimethyl ether, diethyl ether, di-n-propyl ether, dibutyl ether, 1,2-dimethoxyethane, trimethoxyethane, and triethoxyethane. More preferred are 1,4-dioxane, butyl glycidyl ether and 1,2-dimethoxyethane.

As the amylenes, α-amylene, β-amylene, γ-amylene, α-isoamylene and β-isoamylene are preferred. More preferred is β-amylene.

As the esters, those represented by the following formulas are preferred:

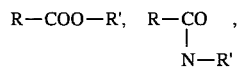

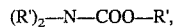

and

RO—R'—COOR"

wherein each of R, R' and R" is a hydrogen atom or a chain or cyclic hydrocarbon group having from 1 to 6 carbon atoms and containing a saturated or unsaturated bond.

Specifically, they include methyl acetate, ethyl acetate, propyl acetate, n-butyl acetate, isobutyl acetate, isopropyl acetate, ethyl acrylate, 2-hydroxyethyl methacrylate, methyl acrylate, butyl acrylate, phenyl acrylate, allyl acrylate, caprolactam, ethyl carbamate, methyl carbamate, and methyl salicylate. More preferred are methyl acetate and methyl salicylate.

As the organic phosphites, those represented by the following formula are preferred:

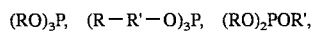

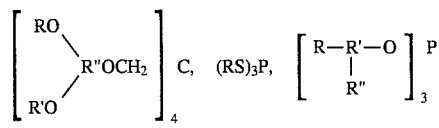

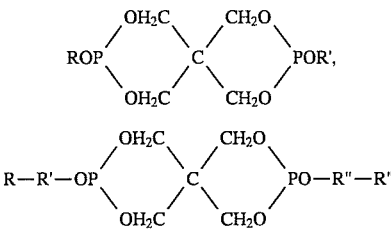

wherein each of R, R', R" and R'" is a hydrogen atom or saturated or unsaturated chain or cyclic hydrocarbon group having from 1 to 18 carbon atoms. Specifically, they include triphenolphosphite, tris(nonylphenyl)phosphite, triethylphosphite, tris(2-ethylhexyl)phosphite, tridecylphosphite, tributylphosphite, diphenylmono(2-ethylhexyl)phosphite, diphenylmonodecylphosphite, diphenylmonotridecylphosphite, dilaurylhydrogen phosphite, diphenylhydrogen phosphite, tetraphenyldipropylene glycol pentaerythritol tetraphosphite, trilauryltrithiophosphite, bis(tridecyl)pentaerythritol diphosphite, bis(nonylphenyl)pentaerythritol diphosphite, tristearyl phosphite, distearyl pentaerythritol diphosphite, and tris(2,4-di-tert-butylphenyl)phosphite. More preferred are triphenylphosphite and tributylphosphite.

As the epoxides, those represented by the following formulas are preferred:

RO 

and

XRO 

wherein R is a saturated or unsaturated chain or cyclic hydrocarbon group having from 1 to 8 carbon atoms, and X is a halogen atom.

Specifically, they include 1,2-butylene oxide, epichlorohydrin, propylene oxide, 2,3-butylene oxide and styrene oxide. More preferred are 1,2-butylene oxide and epichlorohydrin.

As the furans, those represented by the following formulas are preferred:

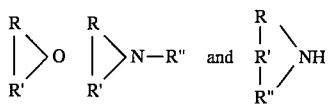

wherein each of R, R' and R" is a saturated or unsaturated hydrocarbon group having from 1 to 2 carbon atoms. Specifically they include tetrahydrofuran, n-methylpyrrole, 2-methylpyrrole and 3-methylpyrrole. More preferred is N-methylpyrrole.

As the alcohols which are mainly used as stabilizers, those presented by the following formulas are preferred:

R—OH, NH$_2$—R—OH, R—O—R'—OH and R—R'—OH wherein each of R and R' is a saturated or unsaturated chain or cyclic hydrocarbon group having from 1 to 6 carbon atoms.

Specifically, they include, methanol, ethanol, sec-butanol, tert-butanol, allylalcohol, benzylalcohol, propanol, isopropanol, tert-amylalcohol, 1-amino-2-propanol, propargylalcohol, isobutanol, butanol, 3-methyl-pentyn-3-ol, 1-methoxy-2-propanol, 3-methyl-1-butyn-3-ol, 2-methyl-3-butyn-3-ol, pentyl alcohol, hexanol, heptanol and octanol. More preferred are sec-butanol and propargyl alcohol.

As the ketones and amides, those represented by the following formulas are preferred:

(R)$_2$CO, R—CO—R', (RNCO)$_2$,

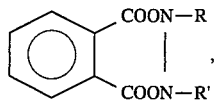

R—CO—NH—R', R—CON—(R')$_2$, (R)$_2$NCON(R')$_2$,

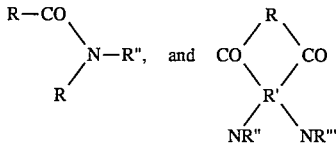

wherein each of R, R', R" and R'" is a hydrogen atom or a saturated or unsaturated hydrocarbon group having from 1 to 4 carbon atoms. Specifically, they include acetone, methyl ethyl ketone, methyl isobutyl ketone, azodicarbonamide, maleic acid hydrazine, phthalic acid hydrazine, formamide, N-methylformamide, N,N-dimethylformamide, N-methylpropropioneamide, 2-pyrrolidone, N,N,N',N'-tetramethylurea and N-methylpyrrolidone. More preferred are methyl isobutyl ketone and 2-pyrrolidone.

As the triazoles, those presented by the following formulas are preferred:

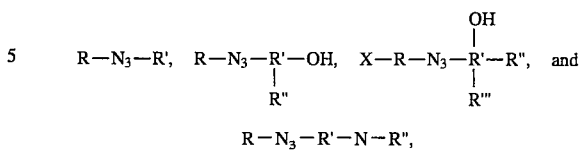

R—N$_3$—R'—N—R", wherein each of R, R', R" and R'" is a hydrogen atom or saturated or unsaturated chain or cyclic hydrocarbon group having from 1 to 16 carbon atoms, and X is a halogen atom.

Specifically, they include 2-(2'-hydroxy-5'-methylphenyl)benzotriazole, 2-(2'-hydroxy-3'-tert-butyl-5'-methylphenyl)-5-chlorobenzotriazole, 1,2,3-benzotriazole, and 1-[(N, N-bis-2-ethylhexyl)aminomethyl]benzotriazole. More preferred is 1,2,3-benzotriazole.

The hydrochlorofluorocarbon azeotropic or azeotropic-like mixture of the present invention is useful for various purposes, for example, as a blowing agent and so on, like conventional CFCs. It is particularly useful as a solvent, since it provides a solvency equivalent or superior to conventional R113. Specific applications as the solvent include a removing agent for flux, grease, oil, wax or ink, a coating solvent, an extracting agent, a cleaning or water-removing agent for various articles made of glass, ceramics, plastic, rubber or metal,. particularly for semiconductor devices, electronic components, electronic circuit boards, electrical devices, precision machine parts or optical lenses. Further, it is useful as a resist developer, a resist-removing agent or a buff polishing and cleaning agent. As a cleaning method, manual wiping, dipping, spraying, shaking, ultrasonic cleaning or vapor cleaning may be employed.

Now, the present invention will be described in further detail with reference to Examples. However, it should be understood that the present invention is by no means restricted by such specific Examples.

EXAMPLES 1 to 152

1,000 g of a mixture as identified in Table 1 was charged in a distillation flask, and using a packed distillation column which contained approximately 20 theoretical plates, distillation was conducted under atmospheric pressure. The fractions thereby obtained were measured by gas chromatography, whereby the presence of an azeotropic composition was found.

On the other hand, the azeotropic-like composition was obtained from the composition after repeating the evaporation and condensation of a mixture as identified in Table 1 for 3 days by an open system cleaning sump.

TEST FOR CLEANING MACHINE OIL

A SUS-304 test piece (25 mm×30 mm×2 mm in thickness) was immersed in machine oil (CQ-30, manufactured by Nippon Sekiyu K.K.) and then immersed in the azeotropic mixture of the present invention for 5 minutes. The results are shown in Table 1, wherein symbol A-⊙ indicates that the machine oil can be removed satisfactorily at the same level as R113.

TEST FOR CLEANING FLUX

A single sided printed circuit board (50 mm×100 mm×1.6 mm in thickness) was coated with a flux (Tamura F-AL-4, manufactured by Tamura Seisakusho) and heated at 200° C. for 2 minutes in a convection oven. Then, it was immersed in the azeotropic mixture of the present invention for one minute. The results are shown in Table 1, in which symbol B-◉ indicates that the flux can be removed satisfactorily at the same level as R113/ethanol=96.2 wt %/3.8 wt %.

TEST FOR REMOVING WATER

A glass plate (30 mm×18 mm×5 mm in thickness) was immersed in deionized water and then immersed in the azeotropic mixture of the present invention for 20 seconds for removal of water. The glass plate withdrawn, was immersed in dry methanol, whereby the removal of water was determined from the increase of the water content in methanol. The results are shown in Table 1, in which symbol C-◉ indicates that the water can be removed satisfactorily at the same level as R113/methanol=93.6 wt %/6.4 wt %.

TABLE 1

| Examples | Mixtures | B.P. (°C.) | Charged composition (wt %) | Boiling point of Azeotrope (°C.) | Azeotropic composition (wt %) | Azeotropic like composition (wt %) | Test results |
|---|---|---|---|---|---|---|---|
| 1 | R225 ca | 51.1 | 30 | 31 | 25 | 5–45 | A-◉ |
|   | R141b | 32 | 70 |   | 75 | 55–95 |   |
| 2 | R225ca | 51.1 | 40 | 44 | 42 | 22–62 | A-◉ |
|   | R113 | 47.6 | 60 |   | 58 | 38–78 |   |
| 3 | R225ca | 51.1 | 80 | 52 | 78 | 58–98 | A-◉ |
|   | R122 | 71.9 | 20 |   | 22 | 2–42 |   |
| 4 | R225ca | 51.1 | 52 | 42 | 50 | 30–70 | A-◉ |
|   | R132b | 46.8 | 48 |   | 50 | 30–70 |   |
| 5 | R225ca | 51.1 | 50 | 34 | 47 | 27–67 | B-◉ |
|   | Dichloromethane | 39.8 | 50 |   | 53 | 33–73 |   |
| 6 | R225cb | 56.1 | 20 | 32 | 16 | 1–36 | A-◉ |
|   | R141b | 32 | 80 |   | 84 | 64–99 |   |
| 7 | R225cb | 56.1 | 50 | 36 | 43 | 33–53 | B-◉ |
|   | Dichloromethane | 39.8 | 50 |   | 57 | 47–67 |   |
| 8 | R225cb | 56.1 | 42 | 43 | 39 | 19–59 | A-◉ |
|   | R132b | 46.8 | 58 |   | 61 | 41–81 |   |
| 9 | R225cb | 56.1 | 80 | 55 | 78 | 58–98 | A-◉ |
|   | R122 | 71.9 | 20 |   | 22 | 2–42 |   |
| 10 | R225cb | 56.1 | 30 | 46 | 32 | 12–52 | A-◉ |
|   | R113 | 47.6 | 70 |   | 68 | 48–88 |   |
| 11 | R244ca | 54 | 15 | 32 | 13 | 1–33 | A-◉ |
|   | R141b | 32 | 85 |   | 87 | 67–99 |   |
| 12 | R244ca | 54 | 50 | 35 | 38 | 18–58 | A-◉ |
|   | Dichloromethane | 39.8 | 50 |   | 62 | 42–82 | B-◉ |
| 13 | R244ca | 54 | 80 | 55 | 83 | 63–99 | A-◉ |
|   | R122 | 71.9 | 20 |   | 17 | 1–37 |   |
| 14 | R244ca | 54 | 42 | 44 | 38 | 18–58 | A-◉ |
|   | R132b | 46.8 | 58 |   | 62 | 42–82 |   |
| 15 | R244ca | 54 | 20 | 47 | 26 | 6–46 | A-◉ |
|   | R113 | 47.6 | 80 |   | 74 | 54–94 |   |
| 16 | R225ca | 51.1 | 70 | 45 | 66 | 46–98 | A-◉ |
|   | Cyclopentane | 49.3 | 30 |   | 34 | 2–54 |   |
| 17 | R225cb | 56.1 | 58 | 47 | 55 | 35–98 | A-◉ |
|   | Cyclopentane | 49.3 | 42 |   | 45 | 2–65 |   |
| 18 | R244ca | 54 | 50 | 50 | 48 | 28–98 | A-◉ |
|   | 2,2-dimethylbutane | 49.7 | 50 |   | 52 | 2–72 |   |
| 19 | R225cb | 56.1 | 25 | 50 | 21 | 11–98 | A-◉ |
|   | 2,2-dimethylbutane | 49.7 | 75 |   | 79 | 2–89 |   |
| 20 | R244ca | 54 | 55 | 47 | 50 | 30–98 | A-◉ |
|   | Cyclopentane | 49.3 | 45 |   | 50 | 2–70 |   |
| 21 | R225cb | 51.1 | 60 | 49 | 56 | 36–98 | A-◉ |
|   | 2,2-dimethylbutane | 49.7 | 40 |   | 44 | 2–64 |   |
| 22 | R225ca | 51.1 | 60 | 47 | 66 | 46–86 | A-◉ |
|   | 2-bromopropane | 59.4 | 40 |   | 34 | 14–54 |   |
| 23 | R225cb | 56.1 | 60 | 49 | 58 | 38–78 | A-◉ |
|   | 2-bromopropane | 59.4 | 40 |   | 42 | 22–62 |   |
| 24 | R244ca | 54 | 50 | 48 | 55 | 35–75 | A-◉ |
|   | 2-bromopropane | 59.4 | 50 |   | 45 | 25–65 |   |
| 25 | R244cb | 58 | 60 | 50 | 50 | 30–70 | A-◉ |
|   | 2-bromopropane | 59.4 | 40 |   | 50 | 30–70 |   |
| 26 | R235ca | 43.9 | 70 | 42 | 74 | 54–94 | A-◉ |
|   | 2-bromopropane | 59.4 | 30 |   | 26 | 6–46 |   |
| 27 | R243cc | 60.2 | 40 | 52 | 50 | 30–70 | A-◉ |
|   | 2-bromopropane | 59.4 | 60 |   | 50 | 30–70 |   |
| 28 | R225cb | 56.1 | 90 | — | — | 50–99 | A-◉ |
|   | 2-methylpentane | 60.3 | 10 |   |   | 1–50 |   |
| 29 | R244ca | 54 | 90 | 55 | 91 | 71–99 | A-◉ |
|   | 2-methylpentane | 60.3 | 10 |   | 9 | 1–29 |   |
| 30 | R244cb | 58 | 70 | 55 | 72 | 52–98 | A-◉ |
|   | 2-methylpentane | 60.3 | 30 |   | 28 | 2–48 |   |
| 31 | R243cc | 60.2 | 70 | 61 | 74 | 54–99 | A-◉ |
|   | 2-methylpentane | 60.3 | 30 |   | 26 | 1–46 |   |
| 32 | R225cb | 56.1 | 80 | 56 | 78 | 58–98 | A-◉ |
|   | 2,3-dimethylbutane | 58.0 | 20 |   | 22 | 2–42 |   |
| 33 | R244ca | 54 | 80 | 53 | 76 | 56–96 |   |

TABLE 1-continued

| Examples | Mixtures | B.P. (°C.) | Charged composition (wt %) | Boiling point of Azeotrope (°C.) | Azeotropic composition (wt %) | Azeotropic like composition (wt %) | Test results |
|---|---|---|---|---|---|---|---|
| | 2,3-dimethylbutane | 58.0 | 20 | | 24 | 4–44 | |
| 34 | R244cb | 58 | 60 | 55 | 63 | 43–95 | A-⊙ |
| | 2,3-dimethylbutane | 58.0 | 40 | | 37 | 5–57 | |
| 35 | R225ca | 51.1 | 90 | — | — | 85–99 | A-⊙ |
| | 2,3-dimethylbutane | 58.0 | 10 | | — | 1–15 | |
| 36 | R243cc | 60.2 | 90 | — | — | 50–95 | A-⊙ |
| | 2,3-dimethylbutane | 58.0 | 10 | | — | 5–50 | |
| 37 | R225ca | 51.1 | 60 | 44 | 57 | 37–77 | A-⊙ |
| | trans-1,2-dichloroethylene | 47.7 | 40 | | 43 | 23–63 | |
| 38 | R225cb | 56.1 | 50 | 46 | 47 | 27–67 | A-⊙ |
| | trans-1,2-dichloroethylene | 47.7 | 50 | | 53 | 33–73 | |
| 39 | R244ca | 54 | 50 | 45 | 46 | 27–66 | A-⊙ |
| | trans-1,2-dichloroethylene | 47.7 | 50 | | 54 | 34–74 | |
| 40 | R244cb | 58 | 45 | 46 | 40 | 20–60 | A-⊙ |
| | trans-1,2-dichloroethylene | 47.7 | 55 | | 60 | 40–80 | |
| 41 | R235ca | 43.9 | 70 | 41 | 66 | 46–86 | A-⊙ |
| | trans-1,2-dichloroethylene | 47.7 | 30 | | 34 | 14–54 | |
| 42 | R243cc | 60.2 | 40 | 45 | 42 | 22–62 | A-⊙ |
| | trans-1,2-dichloroethylene | 47.7 | 60 | | 58 | 38–78 | |
| 43 | R225ca | 51.1 | 80 | 50 | 78 | 58–98 | A-⊙ |
| | cis-1,2-dichloroethylene | 60.6 | 20 | | 22 | 2–42 | |
| 44 | R225cb | 56.1 | 70 | 53 | 69 | 59–79 | A-⊙ |
| | cis-1,2-dichloroethylene | 60.6 | 30 | | 31 | 21–41 | |
| 45 | R244ca | 54 | 70 | 51 | 67 | 47–87 | A-⊙ |
| | cis-1,2-dichloroethylene | 60.6 | 30 | | 33 | 13–53 | |
| 46 | R244cb | 58 | 60 | 54 | 59 | 39–79 | A-⊙ |
| | cis-1,2-dichloroethylene | 60.6 | 40 | | 41 | 21–61 | |
| 47 | R235ca | 43.9 | 90 | 45 | 94 | 74–99 | A-⊙ |
| | cis-1,2-dichloroethylene | 60.6 | 10 | | 6 | 1–26 | |
| 48 | R243cc | 60.2 | 60 | 52 | 58 | 38–78 | A-⊙ |
| | cis-1,2-dichloroethylene | 60.6 | 40 | | 42 | 22–62 | |
| 49 | R244cb | 58 | 10 | 48 | 12 | 2–32 | A-⊙ |
| | R113 | 47.6 | 90 | | 88 | 68–98 | |
| 50 | R235ca | 43.9 | 60 | 42 | 56 | 36–76 | A-⊙ |
| | R113 | 47.6 | 40 | | 44 | 24–64 | |
| 51 | R244cb | 58 | 30 | 36 | 33 | 13–53 | A-⊙ |
| | Dichloromethane | 39.8 | 70 | | 67 | 47–87 | |
| 52 | R235ca | 43.9 | 50 | 32 | 53 | 33–73 | A-⊙ |
| | Dichloromethane | 39.8 | 50 | | 47 | 27–67 | |
| 53 | R243cc | 60.2 | 50 | 38 | 30 | 10–50 | A-⊙ |
| | Dichloromethane | 39.8 | 50 | | 70 | 50–90 | |
| 54 | R244cb | 58 | 40 | 48 | 43 | 23–99 | A-⊙ |
| | Cyclopentane | 49.3 | 60 | | 57 | 1–77 | |
| 55 | R235ca | 43.9 | 80 | 42 | 77 | 67–99 | A-⊙ |
| | Cyclopentane | 49.3 | 20 | | 23 | 1–33 | |
| 56 | R243cc | 60.2 | 25 | 49 | 30 | 10–99 | A-⊙ |
| | Cyclopentane | 49.3 | 75 | | 70 | 1–90 | |
| 57 | R244cb | 58 | 40 | 50 | 34 | 14–99 | A-⊙ |
| | 2,2-dimethylbutane | 49.7 | 60 | | 66 | 1–86 | |
| 58 | R235ca | 43.9 | 80 | 43 | 81 | 61–99 | A-⊙ |
| | 2,2-dimethylbutane | 49.7 | 20 | | 19 | 1–39 | |
| 59 | R244cb | 58 | 80 | 58 | 75 | 55–95 | A-⊙ |
| | R122 | 71.9 | 20 | | 25 | 5–45 | |
| 60 | R244cb | 58 | 30 | 45 | 29 | 9–49 | A-⊙ |
| | R132b | 46.8 | 70 | | 71 | 51–91 | |
| 61 | R235ca | 43.9 | 20 | 28 | 14 | 1–34 | A-⊙ |
| | R123 | 27.1 | 80 | | 86 | 66–99 | |
| 62 | R235ca | 43.9 | 20 | 39 | 57 | 37–77 | A-⊙ |
| | R132b | 46.8 | 80 | | 43 | 23–63 | |
| 63 | R235ca | 43.9 | 30 | 30 | 34 | 14–54 | A-⊙ |
| | R141b | 32 | 70 | | 66 | 46–86 | |
| 64 | R243cc | 60.2 | 80 | 60 | 77 | 57–97 | A-⊙ |
| | R122 | 71.9 | 20 | | 23 | 3–43 | |

TABLE 1-continued

| Examples | Mixtures | B.P. (°C.) | Charged composition (wt %) | Boiling point of Azeotrope (°C.) | Azeotropic composition (wt %) | Azeotropic like composition (wt %) | Test results |
|---|---|---|---|---|---|---|---|
| 65 | R243cc | 60.2 | 20 | 46 | 24 | 4–44 | A-☉ |
|  | R132b | 46.8 | 80 |  | 76 | 56–96 |  |
| 66 | R225ca | 51.1 | 90 | 52 | 95 | 75–99 | A-☉ |
|  | R141 | 75.7 | 10 |  | 5 | 1–25 |  |
| 67 | R225cb | 56.1 | 90 | 56 | 89 | 69–99 | A-☉ |
|  | R141 | 75.7 | 10 |  | 11 | 1–31 |  |
| 68 | R244cb | 58 | 85 | 59 | 90 | 70–99 | A-☉ |
|  | R141 | 75.7 | 15 |  | 10 | 1–30 |  |
| 69 | R225ca | 51.1 | 97 | 46 | 94.6 | 75–99 | A-☉ |
|  | Methanol | 64.5 | 3 |  | 5.4 | 1–25 | B-☉ |
|  |  |  |  |  |  |  | C-☉ |
| 70 | R225cb | 56.1 | 97 | 53.8 | 95.6 | 74–99.5 | A-☉ |
|  | Ethanol | 78.3 | 3 |  | 4.4 | 0.5–26 | B-☉ |
|  |  |  |  |  |  |  | C-☉ |
| 71 | R225cb | 56.1 | 97 | 54.9 | 97.9 | 77–99 | A-☉ |
|  | Isopropanol | 82.4 | 3 |  | 2.1 | 1–23 | B-☉ |
|  |  |  |  |  |  |  | C-☉ |
| 72 | R225cb | 56.1 | 95 | 47.2 | 93.3 | 74–99 | A-☉ |
|  | Methanol | 64.5 | 5 |  | 6.7 | 1–26 | B-☉ |
|  |  |  |  |  |  |  | C-☉ |
| 73 | R225ca | 51.1 | 90 | 50 | 94.8 | 14–98 | A-☉ |
|  | R225cb | 56.1 | 5 |  | 2.7 | 1–85 | B-☉ |
|  | Ethanol | 78.3 | 5 |  | 2.5 | 1–16 | C-☉ |
| 74 | R225ca | 51.1 | 89 | 46 | 89.8 | 14–98 | A-☉ |
|  | R225cb | 56.1 | 6 |  | 5.6 | 1–85 | B-☉ |
|  | Methanol | 64.7 | 5 |  | 4.6 | 1–16 | C-☉ |
| 75 | R225ca | 51.1 | 98.5 | 50 | 97.3 | 75–99.5 | A-☉ |
|  | Ethanol | 78.3 | 1.5 |  | 2.7 | 0.5–25 | B-☉ |
|  |  |  |  |  |  |  | C-☉ |
| 76 | R225ca | 51.1 | — | — | — | 76–99 | A-☉ |
|  | Iso-propanol | 82.4 |  |  |  | 1–24 | B-☉ |
|  |  |  |  |  |  |  | C-☉ |
| 77 | R225ca | 51.1 | 35 | — | 38 | 15–61 | A-☉ |
|  | R113 | 47.6 | 15 |  | 15 | 8–44 | B-☉ |
|  | Dichloromethane | 39.8 | 50 |  | 47 | 34–70 |  |
| 78 | R225cb | 56.1 | 25 | — | 26 | 6–27 | A-☉ |
|  | R113 | 47.6 | 35 |  | 35 | 22–52 |  |
|  | R132b | 46.8 | 40 |  | 39 | 27–51 |  |
| 79 | R225ca | 51.1 | 35 | — | 32 | 22–55 | A-☉ |
|  | R113 | 47.6 | 25 |  | 29 | 10–46 |  |
|  | R132b | 46.8 | 40 |  | 39 | 21–55 |  |
| 80 | R225cb | 56.1 | 25 | — | 26 | 8–38 | A-☉ |
|  | R113 | 47.6 | 25 |  | 24 | 8–47 | B-☉ |
|  | Dichloromethane | 39.8 | 50 |  | 50 | 34–63 |  |
| 81 | R244ca | 54 | 25 | — | 25 | 6–33 | A-☉ |
|  | R113 | 47.6 | 20 |  | 19 | 9–41 | B-☉ |
|  | Dichloromethane | 39.8 | 55 |  | 56 | 43–68 |  |
| 82 | R244ca | 54 | 20 | — | 19 | 4–39 | A-☉ |
|  | R113 | 47.6 | 30 |  | 32 | 6–53 |  |
|  | R132b | 46.8 | 50 |  | 49 | 30–67 |  |
| 83 | R225ca | 51.1 | 40 | — | 41 | 28–52 | A-☉ |
|  | R113 | 47.6 | 20 |  | 22 | 7–39 | B-☉ |
|  | trans-1,2-dichloroethylene | 47.7 | 40 |  | 37 | 25–48 |  |
| 84 | R244ca | 54 | 30 | — | 25 | 8–36 | A-☉ |
|  | R113 | 47.6 | 60 |  | 62 | 48–85 | B-☉ |
|  | 2-bromopropane | 59.4 | 10 |  | 13 | 3–28 |  |
| 85 | R225ca | 51.1 | 40 | — | 42 | 29–60 | A-☉ |
|  | R113 | 47.6 | 50 |  | 47 | 11–61 | B-☉ |
|  | 2-bromopropane | 59.4 | 10 |  | 11 | 3–29 |  |
| 86 | R244ca | 54 | 20 | — | 22 | 4–38 | A-☉ |
|  | R113 | 47.6 | 60 |  | 58 | 40–77 | B-☉ |
|  | cis-1,2-dichloroethylene | 60.6 | 20 |  | 20 | 9–32 |  |
| 87 | R225ca | 56.1 | 35 | — | 32 | 19–43 | A-☉ |
|  | R113 | 47.6 | 50 |  | 53 | 39–60 | B-☉ |
|  | cis-1,2-dichloroethylene | 60.6 | 15 |  | 15 | 8–22 |  |
| 88 | R225ca | 51.1 | 40 | — | 42 | 25–54 | A-☉ |
|  | R113 | 47.6 | 45 |  | 45 | 38–58 | B-☉ |
|  | cis-1,2-dichloroethylene | 60.6 | 15 |  | 13 | 8–22 |  |
| 89 | R244ca | 54 | 35 | — | 34 | 5–45 | A-☉ |
|  | R113 | 47.6 | 22 |  | 20 | 4–60 | B-☉ |
|  | trans-1,2- | 47.7 | 48 |  | 46 | 26–59 |  |

TABLE 1-continued

| Examples | Mixtures | B.P. (°C.) | Charged composition (wt %) | Boiling point of Azeotrope (°C.) | Azeotropic composition (wt %) | Azeotropic like composition (wt %) | Test results |
|---|---|---|---|---|---|---|---|
| | dichloroethylene | | | | | | |
| 90 | R225cb | 56.1 | 35 | — | 36 | 27–51 | A-☉ |
| | R113 | 47.6 | 25 | | 27 | 6–44 | B-☉ |
| | trans-1,2-dichloroethylene | 47.7 | 40 | | 37 | 29–48 | |
| 91 | R225cb | 56.1 | 35 | — | 34 | 22–43 | A-☉ |
| | R113 | 47.6 | 55 | | 56 | 38–68 | B-☉ |
| | 2-bromopropane | 59.4 | 10 | | 10 | 3–26 | |
| 92 | R225cb | 56.1 | 35 | — | 34 | 20–53 | A-☉ |
| | R113 | 47.6 | 55 | | 55 | 8–72 | |
| | Cyclopentane | 49.3 | 10 | | 11 | 1–40 | |
| 93 | R225ca | 51.1 | 40 | — | 41 | 28–65 | A-☉ |
| | R113 | 47.6 | 50 | | 52 | 13–68 | |
| | Cyclopentane | 49.3 | 10 | | 7 | 2–35 | |
| 94 | R225ca | 54 | 25 | — | 23 | 17–46 | A-☉ |
| | R113 | 47.6 | 70 | | 71 | 8–77 | |
| | 2,2-dimethylbutane | 49.7 | 5 | | 6 | 2–56 | |
| 95 | R225ca | 51.1 | 50 | — | 52 | 42–61 | A-☉ |
| | R113 | 47.6 | 20 | | 16 | 7–55 | B-☉ |
| | 1-chloropropane | 46.6 | 30 | | 32 | 2–43 | |
| 96 | R225cb | 56.1 | 40 | — | 42 | 23–44 | A-☉ |
| | R113 | 47.6 | 30 | | 27 | 8–70 | B-☉ |
| | 1-chloropropane | 46.6 | 30 | | 31 | 2–47 | |
| 97 | R244ca | 54 | 20 | — | 22 | 4–33 | A-☉ |
| | R113 | 47.6 | 60 | | 57 | 41.78 | B-☉ |
| | 2-chloro-2-methyl-propane | 50.7 | 20 | | 21 | 8–31 | |
| 98 | R244ca | 54 | 30 | — | 27 | 5–45 | A-☉ |
| | R113 | 47.6 | 50 | | 50 | 9–74 | |
| | Cyclopentane | 49.3 | 20 | | 23 | 12–46 | |
| 99 | R225ca | 51.1 | 45 | — | 40 | 28–56 | A-☉ |
| | R113 | 47.6 | 50 | | 55 | 12–64 | B-☉ |
| | 2-chloro-2-methyl-propane | 50.7 | 5 | | 5 | 2–32 | |
| 100 | R225cb | 56.1 | 30 | — | 31 | 17–38 | A-☉ |
| | R113 | 47.6 | 60 | | 58 | 41–75 | B-☉ |
| | 2-chloro-2-methyl-propane | 50.7 | 10 | | 11 | 2–21 | |
| 101 | R244ca | 54 | 35 | — | 36 | 9–39 | A-☉ |
| | R113 | 47.6 | 20 | | 19 | 9–84 | B-☉ |
| | 1-chloropropane | 46.6 | 45 | | 45 | 2–60 | |
| 102 | R225ca | 51.1 | 90 | — | 90 | 36–97 | A-☉ |
| | R225cb | 56.1 | 5 | | 7 | 1–51 | |
| | 2-methylpentane | 60.3 | 5 | | 3 | 1–16 | |
| 103 | R225ca | 51.1 | 85 | — | 88 | 6–94 | A-☉ |
| | R225cb | 56.1 | 10 | | 8 | 1–83 | |
| | 2,3-dimethylbutane | 58.0 | 5 | | 4 | 1–26 | |
| 104 | R225ca | 51.1 | 50 | — | 50 | 6–67 | A-☉ |
| | R225cb | 56.1 | 10 | | 12 | 4–67 | B-☉ |
| | 2-chloro-2-methyl-propane | 50.7 | 40 | | 38 | 1–58 | |
| 105 | R225ca | 51.1 | 40 | — | 41 | 7–56 | A-☉ |
| | R225cb | 56.1 | 15 | | 14 | 7–61 | B-☉ |
| | 1-chloropropane | 46.6 | 45 | | 45 | 1–54 | |
| 106 | R225ca | 51.1 | 55 | — | 54 | 6–66 | A-☉ |
| | R225cb | 56.1 | 10 | | 10 | 5–64 | B-☉ |
| | 2-bromopropane | 59.4 | 35 | | 36 | 10–48 | |
| 107 | R225ca | 51.1 | 60 | — | 58 | 6–70 | A-☉ |
| | R225cb | 56.1 | 10 | | 12 | 4–74 | B-☉ |
| | cis-1,2-dichloro-ethylene | 60.6 | 30 | | 30 | 10–38 | |
| 108 | R225ca | 51.1 | 40 | — | 42 | 8–57 | A-☉ |
| | R225cb | 56.1 | 15 | | 13 | 6–54 | B-☉ |
| | trans-1,2-dichloro-ethylene | 47.7 | 45 | | 45 | 10–59 | |
| 109 | R225ca | 51.1 | 80 | — | 80 | 40–89 | A-☉ |
| | R225cb | 56.1 | 10 | | 8 | 2–37 | B-☉ |
| | R122 | 71.9 | 10 | | 12 | 3–23 | |
| 110 | R225ca | 51.1 | 80 | — | 84 | 44–92 | A-☉ |
| | R225cb | 56.1 | 10 | | 8 | 2–41 | B-☉ |
| | R141 | 75.7 | 10 | | 8 | 1–17 | |
| 111 | R225ca | 51.1 | 35 | — | 36 | 6–44 | A-☉ |
| | R225cb | 56.1 | 10 | | 11 | 4–44 | B-☉ |
| | R132b | 46.8 | 55 | | 53 | 44–73 | |
| 112 | R225ca | 56.1 | 25 | — | 20 | 8–31 | A-☉ |

TABLE 1-continued

| Examples | Mixtures | B.P. (°C.) | Charged composition (wt %) | Boiling point of Azeotrope (°C.) | Azeotropic composition (wt %) | Azeotropic like composition (wt %) | Test results |
|---|---|---|---|---|---|---|---|
|  | R141b | 32 | 65 |  | 67 | 36–88 | B-⊙ |
|  | Dichloromethane | 39.8 | 10 |  | 13 | 3–38 |  |
| 113 | R225ca | 51.1 | 30 | — | 26 | 8–41 | A-⊙ |
|  | R141b | 32 | 60 |  | 62 | 32–84 | B-⊙ |
|  | Dichloromethane | 39.8 | 10 |  | 12 | 3–31 |  |
| 114 | R225ca | 51.1 | 15 | — | 12 | 6–33 | A-⊙ |
|  | R141b | 32 | 5 |  | 7 | 2–33 | B-⊙ |
|  | R123 | 27.1 | 80 |  | 81 | 44–86 |  |
| 115 | R225ca | 51.1 | 30 | — | 33 | 5–47 | A-⊙ |
|  | R225cb | 56.1 | 10 |  | 9 | 3–42 |  |
|  | R113 | 47.6 | 60 |  | 58 | 5–79 |  |
| 116 | R225ca | 51.1 | 25 | — | 25 | 9–49 | A-⊙ |
|  | R225cb | 56.1 | 21 |  | 21 | 8–39 | B-⊙ |
|  | Dichloromethane | 39.8 | 55 |  | 54 | 5–70 |  |
| 117 | R244ca | 54 | 15 | — | 16 | 6–31 | A-⊙ |
|  | R141b | 32 | 70 |  | 68 | 38–90 | B-⊙ |
|  | Dichloromethane | 39.8 | 15 |  | 16 | 3–40 |  |
| 118 | 244ca | 54 | 20 | — | 21 | 5–58 | A-⊙ |
|  | R225cb | 56.1 | 40 |  | 42 | 7–66 | B-⊙ |
|  | 2-bromopropane | 59.4 | 40 |  | 37 | 5–54 |  |
| 119 | R244ca | 54 | 30 | — | 31 | 4–58 | A-⊙ |
|  | R225cb | 56.1 | 40 |  | 35 | 7–71 | B-⊙ |
|  | cis-1,2-dichloro-ethylene | 60.6 | 30 |  | 34 | 4–43 |  |
| 120 | R244ca | 54 | 15 | — | 15 | 8–58 | A-⊙ |
|  | R225cb | 56.1 | 40 |  | 39 | 9–65 | B-⊙ |
|  | 1-chloropropane | 46.6 | 45 |  | 46 | 5–71 |  |
| 121 | R244ca | 54 | 20 | — | 22 | 7–55 | A-⊙ |
|  | R225cb | 56.1 | 30 |  | 32 | 8–56 | B-⊙ |
|  | 2-chloro-2-methyl-propane | 50.7 | 50 |  | 46 | 5–74 |  |
| 122 | R244ca | 54 | 60 | — | 62 | 29–87 | A-⊙ |
|  | R225cb | 56.1 | 20 |  | 20 | 6–68 |  |
|  | 2,3-dimethylbutane | 58 | 20 |  | 18 | 2–29 |  |
| 123 | R244ca | 54 | 20 | — | 18 | 5–42 | A-⊙ |
|  | R225cb | 56.1 | 20 |  | 24 | 7–50 | B-⊙ |
|  | R132b | 46.8 | 60 |  | 58 | 41–80 |  |
| 124 | R244ca | 54 | 30 | — | 30 | 5–55 | A-⊙ |
|  | R225cb | 56.1 | 25 |  | 26 | 8–57 | B-⊙ |
|  | trans-1,2-dichloro-ethylene | 47.7 | 45 |  | 44 | 5–61 |  |
| 125 | R244ca | 54 | 25 | — | 25 | 8–56 | A-⊙ |
|  | R225cb | 56.1 | 30 |  | 32 | 9–55 |  |
|  | Cyclopentane | 49.3 | 45 |  | 45 | 5–69 |  |
| 126 | R244ca | 54 | 20 | — | 17 | 7–35 | A-⊙ |
|  | R225cb | 56.1 | 20 |  | 24 | 9–42 | B-⊙ |
|  | Dichloromethane | 39.8 | 60 |  | 59 | 45–73 |  |
| 127 | R244ca | 54 | 40 | — | 39 | 7–61 | A-⊙ |
|  | R225ca | 51.1 | 20 |  | 19 | 8–71 |  |
|  | 2,2-dimethylbutane | 49.7 | 40 |  | 42 | 5–72 |  |
| 128 | R244ca | 54 | 10 | — | 12 | 5–41 | A-⊙ |
|  | R225ca | 51.1 | 30 |  | 34 | 9–48 | B-⊙ |
|  | Dichloromethane | 39.8 | 60 |  | 54 | 40–73 |  |
| 129 | R244ca | 54 | 10 | — | 9 | 2–37 | A-⊙ |
|  | R225ca | 51.1 | 40 |  | 40 | 7–50 | B-⊙ |
|  | R132b | 46.8 | 50 |  | 51 | 35–72 |  |
| 130 | R244ca | 54 | 25 | — | 24 | 3–49 | A-⊙ |
|  | R225ca | 51.1 | 70 |  | 70 | 47–95 | B-⊙ |
|  | R141 | 75.7 | 5 |  | 6 | 0.1–17 |  |
| 131 | R244ca | 54 | 10 | — | 11 | 5–55 | A-⊙ |
|  | R225ca | 51.1 | 55 |  | 55 | 9–67 |  |
|  | Cyclopentane | 49.3 | 35 |  | 34 | 3–53 |  |
| 132 | R244ca | 54 | 20 | — | 21 | 3–59 | A-⊙ |
|  | R225ca | 51.1 | 70 |  | 70 | 36–93 | B-⊙ |
|  | R122 | 71.9 | 10 |  | 9 | 1–22 |  |
| 133 | R244ca | 54 | 10 | — | 11 | 3–69 | A-⊙ |
|  | R225ca | 51.1 | 50 |  | 47 | 8–78 | B-⊙ |
|  | trans-1,2-dichloro-ethylene | 47.7 | 40 |  | 42 | 3–54 |  |
| 134 | R244ca | 54 | 8 | — | 10 | 3–59 | A-⊙ |
|  | R225ca | 51.1 | 62 |  | 60 | 7–75 | B-⊙ |
|  | cis-1,2-dichloro-ethylene | 60.6 | 30 |  | 30 | 3–38 |  |
| 135 | R244ca | 54 | 10 | — | 8 | 3–58 | A-⊙ |
|  | R225ca | 51.1 | 60 |  | 58 | 6–71 | B-⊙ |

TABLE 1-continued

| Examples | Mixtures | B.P. (°C.) | Charged composition (wt %) | Boiling point of Azeotrope (°C.) | Azeotropic composition (wt %) | Azeotropic like composition (wt %) | Test results |
|---|---|---|---|---|---|---|---|
| | 2-bromopropane | 59.4 | 30 | | 34 | 3–44 | |
| 136 | R244ca | 54 | 45 | — | 47 | 22–86 | A-⊙ |
| | R225cb | 56.1 | 45 | | 47 | 6–72 | A-⊙ |
| | R141 | 75.7 | 10 | | 6 | 1–21 | |
| 137 | R225ca | 51.1 | 50 | — | 48 | 10–88 | A-⊙ |
| | R225cb | 56.1 | 10 | | 15 | 8–70 | |
| | Cyclopentane | 49.3 | 40 | | 37 | 3–58 | |
| 138 | R244ca | 54 | 50 | — | 45 | 8–83 | A-⊙ |
| | R225cb | 56.1 | 40 | | 45 | 6–84 | B-⊙ |
| | R122 | 71.9 | 10 | | 10 | 3–28 | |
| 139 | R244ca | 54 | 30 | — | 29 | 3–84 | A-⊙ |
| | R225ca | 51.1 | 65 | | 67 | 13–94 | |
| | 2,3-dimethylbutane | 58 | 5 | | 4 | 0.1–19 | |
| 140 | R244ca | 54 | 10 | — | 11 | 3–48 | A-⊙ |
| | R225ca | 51.1 | 50 | | 48 | 7–62 | B-⊙ |
| | 1-chloropropane | 46.6 | 40 | | 41 | 3–56 | |
| 141 | R244ca | 54 | 10 | — | 10 | 3–56 | A-⊙ |
| | R225ca | 51.1 | 60 | | 54 | 6–72 | B-⊙ |
| | 2-chloro-2-methyl-propane | 50.7 | 30 | | 36 | 3–54 | |
| 142 | R244ca | 54 | 45 | — | 42 | 7–76 | A-⊙ |
| | R225cb | 56.1 | 10 | | 14 | 8–62 | |
| | 2,2-dimethylbutane | 49.7 | 45 | | 44 | 3–73 | |
| 143 | R244ca | 54 | — | — | — | 76–99 | A-⊙ |
| | Methanol | 64.7 | | | | 1–24 | B-⊙ |
| 144 | R244ca | 54 | — | — | — | 77–99 | A-⊙ |
| | Ethanol | 78.3 | | | | 1–23 | B-⊙ |
| 145 | R244ca | 54 | — | — | — | 79–99 | A-⊙ |
| | Isopropanol | 82.4 | | | | 1–21 | B-⊙ |
| 146 | R225ca | 51.1 | — | — | — | 50–80 | |
| | R244ca | 54 | | | | 10–40 | A-⊙ |
| | Ethanol | 78.3 | | | | 1–10 | B-⊙ |
| 147 | R225cb | 56.1 | — | — | — | 40–80 | |
| | R224ca | 54 | | | | 10–50 | A-⊙ |
| | Ethanol | 78.3 | | | | 1–10 | B-⊙ |
| 148 | R225ca | 51.1 | — | — | — | 5–99 | |
| | R225cb | 56.1 | | | | 3–99 | A-⊙ |
| | R244ca | 54 | | | | 1–69 | B-⊙ |
| | Ethanol | 78.3 | | | | 1–35 | |
| 149 | R225ca | 51.1 | — | — | — | 50–80 | A-⊙ |
| | R244ca | 54 | | | | 10–40 | B-⊙ |
| | Methanol | 64.7 | | | | 1–10 | |
| 150 | R225cb | 56.1 | — | — | — | 40–80 | A-⊙ |
| | R244ca | 54 | | | | 10–50 | B-⊙ |
| | Methanol | 64.7 | | | | 1–10 | |
| 151 | R225ca | 51.1 | — | — | — | 5–99 | A-⊙ |
| | R225cb | 56.1 | | | | 3–99 | B-⊙ |
| | R244ca | 54 | | | | 1–69 | |
| | Methanol | 64.7 | | | | 1–35 | |
| 152 | R225ca | 51.1 | — | — | — | 1–98 | A-⊙ |
| | R225cb | 56.1 | | | | 1–98 | B-⊙ |
| | Isopropanol | 82.4 | | | | 1–16 | |

REFERENCE EXAMPLES

For the purpose of ascertaining the effects of the azeotropic-like mixture of the present invention for stabilization, the following test was applied to the mixture as identified in Table 2.

In accordance with JIS K1600, a metal test piece was placed in both the liquid phase portion and the gas phase portion of the stabilized mixture as identified in Table 2, and after 48 hours, the state of corrosion of the test piece was inspected. The results are shown in Table 2.

Azeotropic-like Mixture

AA: R225ca/R225cb/methanol=47 wt %/47 wt %/6 wt %

Stabilizer

NM: Nitromethane
DIPA: Diisopropylamine
Am: β-Amylene
TPH: Triphenylphosphite
DME: 1,2-Dimethoxyethane
s-Bu: sec-Butanol
ECH: Epichlorohydrin
BHT: 2,6-Di-t-butyl-o-cresol
BTA: 1,2,3-Benzotriazole PH: Phenol
DO: 1,4-Dioxane
MeA: Methyl acetate
BO: 1,2-Buthyleneoxide
MP: N-methylpyrrole
MIBK: Methyl isobutyl ketone
i-Bu: Isobutanol -continued Appearance of test piece ◎: No corrosion　　　　　○: No substantial corrosion
Δ: Corrosion slightly observed
X: Substantial corrosion observed.

TABLE 2

| Reference Examples | Stabilized mixture (wt %) | Corrosion of test piece | | |
|---|---|---|---|---|
| | | Fe | Cu | Ag |
| AA01 | AA(99.5)/PH(0.5) | ◎ | ○ | ○ |
| AA02 | AA(99.5)/DIPA(0.5) | ◎ | ○ | ○ |
| AA03 | AA(99.5)/Am(0.5) | ◎ | ○ | ○ |
| AA04 | AA(99.5)/TPH(0.5) | ◎ | ○ | ○ |
| AA05 | AA(99.5)/MP(0.5) | ◎ | ○ | ○ |
| AA06 | AA(99.5)/BTA(0.5) | ○ | ◎ | ○ |
| AA07 | AA(99)/NM(1) | ◎ | ○ | ○ |
| AA08 | AA(99)/DO(1) | ◎ | ○ | ○ |
| AA09 | AA(99)/MeA(1) | ◎ | ○ | ○ |
| AA10 | AA(99)/BO(1) | ◎ | ○ | ○ |
| AA11 | AA(99)/DME(1) | ◎ | ○ | ○ |
| AA12 | AA(99)/s-Bu(1) | ◎ | ○ | ○ |
| AA13 | AA(99)/MIBK(1) | ◎ | ○ | ○ |
| AA14 | AA(99)/ECH(1) | ◎ | ○ | ○ |
| AA15 | AA(98.5)/NM(1)/BTA(0.5) | ◎ | ◎ | ◎ |
| AA16 | AA(97.5)/NM(1)/BO(1)/BHT(0.5) | ◎ | ◎ | ○ |
| AA17 | AA(97)/NM(1)/BO(1)/BHT(0.5/BTA(0.5) | ◎ | ◎ | ◎ |
| AA18 | AA(96)/NM(1)/BTA(0.5)BO(1)/i-Bu(1)/BHT(0.5) | ◎ | ◎ | ◎ |
| Comparative Example | AA(100) | ◎ | Δ | Δ |

INDUSTRIAL APPLICABILITY

The hydrochlorofluorocarbon azeotropic or azeotropic-like mixture of the present invention is non-flammable or hardly flammable and has excellent properties equal or superior to conventional CFCs. Further, the mixture shows no substantial change in the composition during boiling and evaporating, since it has an azeotropic composition or an azeotropic-like composition, and it can be used in the same manner as a conventional single CFC and thus has a merit that it requires no substantial change of the conventional technique. Further, it is excellent in the properties for dissolving and removing a flux or oil like R113 which is commonly used as a solvent, and thus it is useful as a cleaning agent which may be an alternative for R113.

We claim:

1. A hydrochlorofluorocarbon azeotropic like mixture consisting essentially of from 75 to 99 weight percent 1,1-dichloro-2,2,3,3,3-pentafluoropropane and from 1 to 25 weight percent methanol which boils at about 46° C. at atmospheric pressure; or from 75 to 99.5 weight percent 1,1-dichloro-2,2,3,3,3-pentafluoropropane and from 0.5 to 25 weight percent ethanol which boils at about 50° C. at atmospheric pressure; or from 74 to 99 weight percent 1,3-dichloro-1,1,2,2,3-pentafluoropropane and from 1 to 26 weight percent methanol which boils at about 47.2° C. at atmospheric pressure; or from 74 to 99.5 weight percent 1,3-dichloro-1,1,2,2,3-pentafluoropropane and from 0.5 to 26 weight percent ethanol which boils at about 53.8° C. at atmospheric pressure; or from 77 to 99 weight percent 1,3-dichloro-1,1,2,2,3-pentafluoropropane and from 1 to 23 weight percent isopropanol which boils at about 54.9° C. at atmospheric pressure;

wherein the components of each azeotropic like composition consists of either 1,1-dichloro-2,2,3,3,3-pentafluoropropane or 1,3-dichloro-1,1,2,2,3-pentafluoropropane and either methanol, ethanol or isopropanol.

2. A hydrochlorofluorocarbon azeotropic mixture consisting essentially of 94.6 weight percent 1,1-dichloro-2,2,3,3,3-pentafluoropropane and 5.4 weight percent methanol which boils at 46° C. at atmospheric pressure; or 97.3 weight percent 1,1-dichloro-2,2,3,3,3-pentafluoropropane and 2.7 weight percent ethanol which boils at 50° C. at atmospheric pressure; or 93.3 weight percent 1,3-dichloro-1,1,2,2,3-pentafluoropropane and 6.7 weight percent methanol which boils at 47.2° C. at atmospheric pressure; or 95.6 weight percent 1,3-dichloro-1,1,2,2,3-pentafluoropropane and 4.4 weight percent ethanol which boils at 53.8° C. at atmospheric pressure; or 97.9 weight percent 1,3-dichloro-1,1,2,2,3-pentafluoropropane and 2.1 weight percent isopropanol which boils at 54.9° C. at atmospheric pressure; wherein the components of each azeotropic composition consists of either 1,1-dichloro-2,2,3,3,3-pentafluoropropane or 1,3-dichloro-1,1,2,2,3-pentafluoropropane and either methanol, ethanol or isopropanol.

3. An azeotropic composition consisting essentially of $CF_3CF_2CHCl_2$ (225ca), $CClF_2CF_2CHClF$ (225cb) and methanol, in amounts, by weight of 89.8 percent, 5.6 percent and 4.6 percent, respectively which boils at about 46° C. at atmospheric pressure.

4. An azeotropic composition consisting essentially of $CF_2CF_2CHCl_2$ (225ca), $CClF_2CF_2CHClF$ (225cb) and ethanol, in amounts, by weight of 94.8 percent, 2.7 percent and 2.5 percent, respectively which boils at about 50° C. at atmospheric pressure.

* * * * *